(12) United States Patent
White et al.

(10) Patent No.: US 6,376,573 B1
(45) Date of Patent: *Apr. 23, 2002

(54) POROUS BIOMATERIALS AND METHODS FOR THEIR MANUFACTURE

(75) Inventors: Eugene W. White, Rossiter, PA (US); Jack C. Debes, Carlsbad, CA (US); Clayton G. Harris, Irvine, CA (US); Edwin C. Shors, Costa Mesa, CA (US)

(73) Assignee: Interpore International, Irvine, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/659,879

(22) Filed: Jun. 7, 1996

Related U.S. Application Data

(63) Continuation-in-part of application No. 08/360,269, filed on Dec. 21, 1994, now abandoned.

(51) Int. Cl.[7] .............................. A61K 2/00; A61K 6/08
(52) U.S. Cl. ........................ 523/115; 523/116; 623/10; 623/11; 623/12; 623/16
(58) Field of Search ...................... 606/76, 77; 424/426, 424/423, 602; 523/115, 116; 623/10, 11, 12, 16

(56) References Cited

U.S. PATENT DOCUMENTS

| | | | | |
|---|---|---|---|---|
| 4,655,777 A | * | 4/1987 | Dunn et al. | 623/16 |
| 5,007,930 A | * | 4/1991 | Dorman et al. | 623/16 |
| 5,084,051 A | * | 1/1992 | Tormala et al. | 606/77 |
| 5,338,772 A | * | 8/1994 | Bauer et al. | 523/115 |
| 5,355,898 A | * | 10/1994 | Ripamonti | 128/898 |
| 5,518,680 A | * | 5/1996 | Cima et al. | 264/401 |
| 5,626,861 A | * | 5/1997 | Laurencin et al. | 424/426 |

FOREIGN PATENT DOCUMENTS

| | | | | |
|---|---|---|---|---|
| WO | 89/00842 | * | 2/1989 | 623/16 |

* cited by examiner

*Primary Examiner*—Thurman K. Page
*Assistant Examiner*—Humera N. Sheikh
(74) *Attorney, Agent, or Firm*—Robert D. Katz; Cooper & Dunham LLP

(57) ABSTRACT

An improved porous ceramic biomaterial is disclosed in which a polymer such as polylactic acid is polymerized in situ to fill the micropores substantially without filling the macropores. The polymer reinforcement helps improve the strength of the implant while preserving its ability to support ingrowth of bone to help integrate the implant into its surgical environment.

27 Claims, 5 Drawing Sheets

POROUS BIOMATERIALS AND METHODS FOR THEIR MANUFACTURE

This is a continuation-in-part of U.S. patent application Ser. No. 08/360,269, filed Dec. 21, 1994 now abandoned. The entire contents of that application are incorporated herein by reference.

FIELD OF INVENTION

This invention relates to improved porous ceramic based biomaterials, and methods for making such materials, and implants fashioned therefrom. In particular, this invention relates to methods of impregnating porous hydroxyapatite with polymeric materials such that when the resultant composite materials are used in prosthetic devices and implants, strength of the implant is enhanced and the interconnected macropores are retained.

BACKGROUND OF INVENTION

Porous Echinoderm and Scleractinian skeletal material has a unique carbonate structure. These materials are permeable with a uniform three dimensional, highly interconnected porosity. The microstructure of this material resembles cancellous bony tissue or bone. The similarity of these invertebrate skeletal materials in microstructure to bone makes them potentially highly useful as bone substitutes. Porites or Goniopera skeleton will resorb or degrade too rapidly to assure bone ingrowth. The natural carbonate skeletal materials, however, such as the calcite of Echinoid spine, or the aragonite skeletons are too brittle for many applications. This brittleness makes the natural carbonates particularly difficult to shape. They also lack the strength and durability required for some bone substitute applications.

A technique was developed to convert the aforementioned calcium carbonate materials into hydroxyapatite, while at the same time retaining the unique microstructure of the coral material. U.S. Pat. No. 3,929,971 (Roy) (incorporated herein by reference) discloses a hydrothermal exchange reaction for converting the porous carbonate coralline skeletal material into hydroxyapatite having the same microstructure as the carbonate skeletal starting material. These synthetic hydroxyapatite materials have been produced commercially for some time and are available from Interpore International, Irvine, Calif. under the trademark Interpore® Implant 200 (derived from coral of the genus Porites and having an average pore diameter of about 200 microns) and under the trademark ProOsteon® Implant 500 (derived from certain members of the family Goniopora and having an average pore diameter of about 500 microns).

Interpore® 200 and ProOsteon® Implant 500, also referred to as Replamineform hydroxyapatite and coralline hydroxyapatite, have been found to be useful as bone substitute materials in dental and surgical applications. These materials are essentially non-degradable, yet biocompatible, and resemble the microstructure of animal and human bone. The porosity of these coral derived materials has been characterized as polymodal by means of scanning electron microscope and mercury porosimetery. The macroporosity is characterized by macropores of 100–1000 µm. The microporosity is characterized by spaces between crystallites on the order of 0.1 µm and larger micropores on the order of 1 µm. More information concerning these materials can be found in the article by Drs. Eugene W. White and Edwin C. Shors entitled "Biomaterial Aspects of Interpore-200® Porous Hydroxyapatite," which appeared in *Dental Clinics of North America*, Vol. 30, January 1986, pp. 49–67, incorporated herein by reference. While calcium phosphates such as Interpore®200, and ProOsteon® Implant 500 are desirable for many applications, and promote the ingrowth of bone and other tissue into and around the implant, they do not satisfy all of the needs of surgeons using them as bone replacements or implants. U.S. Pat. No. 4,976,736 (White and Shors) (incorporated by reference) also discloses biomaterials useful for orthopedic and dental applications in which two rates of degradation are sought. To accomplish this, the inventors disclose a biomaterial (and method for making such a biomaterial) which has a base portion of calcium carbonate and a surface layer of calcium phosphate or hydroxyapatite. The biomaterial may be machined into various shapes and sizes for orthopedic and dental applications. The biomaterial presents an interface of hydroxyapatite to tissue and body fluids at the site of the surgical defect. The unreacted carbonate behind the interface gradually gets replaced by new bone ingrowth, thereby more completely filling the implant site with the body's own bone material. In one embodiment mentioned in that patent, the macroporosity of the composite is filed with synthetic polymer such as polysulfone, polyethylene, silicone rubber or polyurethane, either with positive injection pressure or by vacuum impregnation. After solification of the polymer, the carbonate may optionally be dissolved away with 10acetic acid, leaving behind the polymer that filled the pores.

Porous ceramics can also be manufactured using a variety of other methods. These ceramics, also made from calcium phosphates, can be used as bone graft substitutes. However, they also have mechanical limitations due to the porosity and to the brittle nature of ceramics. Some of these ceramics have microporosity in addition to macroporosity. Examples include U.S. Pat. Nos. 5,348,788; 5,455,100; and 5,487,933.

Tencer et al., in an article entitled, "Bone Ingrowth Into Polymer Coated Porous Synthetic Coralline Hydroxyapatite," *J. Orth. Res.* pp. 275–82 (1987), discusses dip-coating the macroporosity or large pores of a coralline hydroxyapatite sample with a polylactic acid (DL-PLA) dilactic-polylactic acid polymer by dipping blocks for 5 seconds in a high (3:1), medium (10:1), or low (30:1) viscosity solution of DL-PLA in chloroform.

The authors state that they achieved a three-fold increase in compressive strength over untreated samples. This treatment, however, tends to fill the macroporosity and obscures or fills the surface openings of the macropores, which limits the rate and amount of bone ingrowth.

An effective means of increasing the strength of coralline hydroxyapatite, while maintaining an open macroporosity for bone ingrowth, has yet to be described. It is therefore an object of the invention to provide bone substitute or implant materials derived from coral or synthetic calcium phosphate ceramics for bone incorporation which preserves the unique porous macrostructure and surface properties thereof, while providing increased strength.

SUMMARY OF THE INVENTION

The disadvantages of the foregoing prior biomaterials are overcome and the foregoing and other objects are achieved by providing an improved method for manufacturing a ceramic based biomaterial with polymer infiltrated micorpores. The process includes infiltrating the porous ceramic biomaterial with a monomer mixture or solution, and perhaps a catalyst if necessary, and treating the resulting material under conditions which cause the monomer to polymerize in situ within the microporosity of the biomaterial, thus strengthening the material and giving it other useful properties.

The invention also provides as a biomaterial a calcium phosphate (hydroxyapatite) structure having a substantially uniform three dimensional macroporosity connected with an interior surface of the biomaterial. The porosity includes interconnected macropores having diameters in the range from about 100 microns to about 1000 microns. The micorporosity of the ceramic biomaterial is infiltrated by a monomer or prepolymer, a catalyst if necessary, and then polymerized such that the polymer fills (or mostly fills) the microporosity of the biomaterial, substantially without filling the macropores therein. For example, monomers of DL-lactide, L-lactide, or glycolide or co-monomers thereof, at or above their melting point can infiltrate the microporosity of coralline hydroxyapatite materials, and then in the presence of a suitable catalyst be thermally polymerized in situ to yield composite materials of increased strength and durability. This is possible due to the low viscosity of the molten monomers combined with adequate capillary action of the microporous spaces. Using this method, strength increases of more than three-fold over the untreated material have been realized, without disrupting the necessary avenues for bone ingrowth.

In another aspect, the invention provides a method for making an improved biomaterial comprising the steps of providing a coralline calcium carbonate material and converting this material to a porous calcium phosphate (or hydroxyapatite) structure by reacting the calcium carbonate structure under heat and pressure in the presence of a synthetic phosphate; and strengthening the porous hydroxyapatite structure by suffusing the interstices of the microporosity with a monomer solution so that the monomer only lightly coats (but does not fill) the interior walls of the macroporosity of the porous hydroxyapatite structure, and then polymerizing the monomer, preferably in the presence of a catalyst.

BRIEF DESCRIPTION OF THE DRAWINGS

Further features, objects, and advantages of the invention maybe understood by reference of the following detailed description of the preferred embodiments taken in conjunction with the drawings in which.

DETAILED DESCRIPTION OF THE PREFERRED EMBODIMENTS

Figure 1:
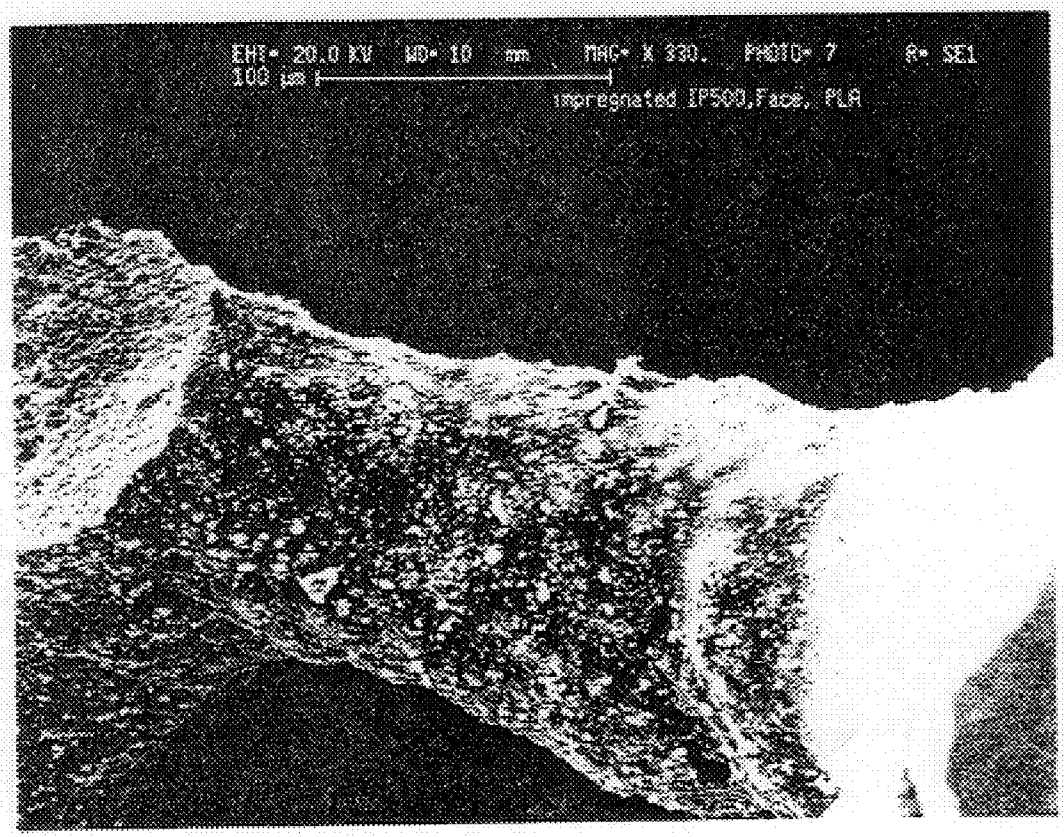
FIG. 1 is a photomicrograph (330×magnification) of a section of a porous hydroxyapatite sample infiltrated with a biopolymer in accordance with the present invention.

The biocompatibility of hydroxyapatite is well established and it is available in dense and porous forms. Coralline hydroxyapatite is widely used as a bone substitute material in oral, periodontal and craniofacial surgery, and has recently been approved for various orthopedic applications, such as bone replacements due to trauma. Other applications are under consideration or investigation. Porous hydroxyapatite promotes bone ingrowth in and around the implant.

In accordance with the present invention, the calcium carbonate making up the microstructure of porous permeable animal skeletal material, e.g., the porous skeletal material of marine invertebrates, such as echinoid spine calcite, Porites skeletal aragonite and Goniopora skeletal aragonite (both calcite and aragonite being carbonates), is converted into whitlockite and hydroxyapatite by hydrothermal chemical exchange with a phosphate donor. The resulting synthetic phosphate (hydroxyapatite or whitlockite) converted skeletal material possesses substantially the same macroporosity (~100–1000, $\mu$m pore diameter) of the original carbonate skeletal material from which it was derived, and preserves intact the interconnecting porosity which provides channels and interstices for bone and tissue ingrowth. These synthetic materials are useful for the manufacture of posthetic devices, such as body and bone implants, tooth fixation, massive hard tissue replacements and the like, since hydroxyapatite and whitlockite are biocompatible materials.

The synthetic phosphate materials prepared in accordance with this invention, as indicated hereinabove, are particularly useful as biomaterials for use in the manufacture of prosthetic devices or for use as implants in human hard tissue and the like. The surface of the materials of this invention, particularly those made from porous carbonate (aragonite) skeletal material of marine life, since they are comprised predominantly of hydroxyapatite $Ca_{10}(PO_4)_6(OH)_2$ with some carbonate present, approximate the carbonate composition of the inorganic component of hard human bone tissue. This hydroxyapatite surface has osteophilic and osteoconductive properties, and helps promote the growth of bone tissue into the porosity or voids in the biomaterial.

Materials of the present invention preferably have a microstructure which is macroporous, completely interconnected, approximating the same pore size as cancellous human bone which would allow permeation of body fluids and blood cells thereinto. Preferably the material includes at least some macropores communicating with the exterior surface of the implant, that is pores of sufficient size to allow infiltration of blood vessels and other tissues and nutrients necessary to form calcified bone tissue therein. The material also includes micropores, which are pores too small in diameter to permit ingrowth of calcified bone tissue. The present invention contemplates strengthening the material by infiltrating, and perhaps filling, the microporosity within the biomaterial while leaving macroporous passageways substantially unfilled and available for bone tissue ingrowth. Materials in accordance with this invention could be prepared which would be suitable for filling bony defects to stimulate bone formation. Applications are for bone reconstruction of the maxilla and mandible, where it would permit rapid ingrowth of hard tissue, as well as other bone repair functions such as segmental bone replacements for bone fractures, tumors, joint surgery and spinal fusion.

As indicated, various porous carbonate skeletal materials, particularly porous carbonate marine skeletal material, may be employed in the practice of this invention. Particularly useful, because of the vast quantities available, is the carbonate skeletal material of scleractinian coral Porites. This skeletal material is composed of the calcium carbonate (aragonite), and the average pore size is approximately 200 microns. Other corals of the genera Goniopora, Alveopora, Acropora and others may be suitably employed in the practice of this invention as the source of the calcium carbonate skeletal material for conversion by hydrothermal chemical exchange with a phosphate into hydroxyapatite. Goniopora has an average pore size of about 500 microns, and includes macropores ranging in size from 5 microns to about 1000 microns, making it suitable for orthopedic uses where larger amounts of bone and tissue ingrowth might be beneficial.

Where the carbonate skeletal material is made up of a calcite carbonate marine skeletal material, and where the calcite contains a substantial amount of magnesium associated therewith the hydrothermal chemical exchange produces whitlockite with a phosphate on the surface of the biomaterial. Both materials, however, hydroxyapatite and whitlockite, are useful materials, with the hydroxyapatite being preferred for the manufacture of human implants, such bone fillers and replacements and the like. Alternatively, the biomaterials of the present invention can be made in the form of porous hydroxyapatite (or whitlockite) granules. These granules can be dispensed into a cavity where bone repair is desired using a syringe adapted to deliver the particles into the cavity. The irregular surfaces of the particles create spaces between adjacent ones, permitting bone and other tissue to grow around the particles, and into their pores. The particles of the present invention are particularly useful for dental applications such as reconstruction of the alveolar ridge and for filling periodontal spaces. For periodontal use, granules having an average nominal diameter of about 425–600 microns and an average pore size of about 200 microns should be used; for reconstruction of the alveolar ridge, granules having an average nominal diameter of about 425 to 1000 microns and an average pore size of about 500 microns can be used. For orthopedic applications, larger granules having an average nominal diameter of 1–4 mm or 4–8 mm can be used, as can be blocks, right cylinders, or other appropriate geometric shapes and sizes. For some applications, it may be desirable to use as a starting material hydroxyapatite coated porous carbonate biomaterial such as one made in accordance with the method discussed in U.S. Pat. No. 4,976,736.

In the manufacture of the synthetic materials of this invention it would be desirable, before subjecting the naturally occurring porous carbonate skeletal material to hydrothermal chemical exchange with a phosphate, to first prepare the porous carbonate skeletal material by the removal of any organic material therefrom. A suitable technique for the removal of organic material from the porous skeletal material would be by immersion in a dilute (about 5%) aqueous solution of sodium hypochlorite. Usually an immersion time of about 30 hours removes substantially all of the organic matter. Following this the material is rinsed, preferably in deionized water, and dried, such as at a temperature of about 90° C. Any suitable technique for the removal of organic material, such as that described in SCIENCE, 119, 771 (1954), might be employed. If desired, the organic-free carbonate skeletal material after conversion by hydrothermal chemical exchange with a phosphate to hydroxyapatite, may be shaped into a desired form or structure, for example, cylinders, screws, nuts, bolts, pins, flat or curved plates and the like.

The conversion of porous carbonate skeletal materials into the improved phosphate biomaterials for the present invention preferably involves lower temperature and pressures than those disclosed in U.S. Pat. No. 3,929,971. The conversion may be carried out by placing blocks or granules of calcium carbonate in phosphate solution or by freeze drying the phosphate onto the carbonate base and then carrying out the hydroconversion in a steam filled autoclave. Preferred temperature range from about 200°–250° C., with about 225°–240° C. appearing optimum. Preferably, the pressure should be that developed in a sealed vessel or autoclave by the gaseous components contained therein, which is estimated to be about 500 to about 4000 p.s.i. If the conversion is carried out in a phosphate solution, such as ammonium phosphate, the temperature should preferably be about 235° C. and the pressure should be preferably about 2000 p.s.i., and the reaction should be carried out for about 10 to about 60 hours.

The chemical reaction involved in the conversion of calcium carbonate to hydroxyapatite is as follows:

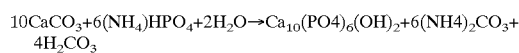
$$10CaCO_3 + 6(NH_4)HPO_4 + 2H_2O \rightarrow Ca_{10}(PO4)_6(OH)_2 + 6(NH4)_2CO_3 + 4H_2CO_3$$

Various substantially water-soluble phosphates may be employed as the phosphate contributing reactant in the hydrothermal chemical exchange reaction to produce the special materials of this invention. The preferred phosphates include ammonium phosphates or orthophosphates. Also useful would be the calcium orthophosphates and the acid phosphates, as well as orthophosphoric acid including its hydrates and derivatives and mixtures of a weak acid, such as acetic acid, with a phosphate.

Upon completion of the hydrothermal chemical exchange reaction, it has been shown by examination including optical microcopy and scanning electorn microscopy, that the resulting three-dimensional completely interpenetrating porous structure is the same as the original carbonate structure form which it was derived. The original calcium carbonate (aragonite) crystal structure of the resulting produced material is absent as determined by x-ray diffraction and by optical microscopy.

Materials exhibiting similar chemistry and morphology have been produced synthetically through various means including those described in U.S. Pat. Nos. 5,348,788, 5,455,100, and 5,487,933 (White) as well as through the use of reticulated foam ceramics.

One biopolymer useful in the present invention is gelatin, derived from high purity collagen by steam autoclaving collagen in aqueous solution at strength ranging from about 3% to about 30% by weight in water for injection or distilled water. Other biopolymers useful herein include those which can be made in solutions or gels of sufficient concentration to infiltrate and perhaps fill or mostly fill the microporosity in the porous hydroxyapatite structure. These biopolymers include collagen (naturally derived or genetically engineered), polyglycolic acid, polylactic acid and its copolymers such as L-lactide coglycolide or DL-lactide coglycolide.

Preferably, the solvent for the gelatin biopolymers is water. This affords several advantages including lack of toxicity. Also, solvent removal (drying) and crosslinking (discussed in more detail below) can be achieved by air-drying at room temperature. This decreases solvent and polymer migration, and avoids use of more problematic crosslinking methods such as radiation and glutaraldehyde.

In preparing coralline hydroxyapatite blocks strengthened with gelatin, two different methods were used to apply the gel solution to the hydroxyapatite. The first method was to pipette lines of solution along the top surface of IP500 blocks to precisely control the amount of gel solution added and to minimize the tendency for the solution to fill macropores and form macropore-bridging bubble films. However, the gelatin tended to stay localized in a trough shaped area near the application "line" and did not equilibrate evenly throughout the blocks even though the blocks appeared to have become uniformly moistened.

The second, and more preferred method, is to preheat the blocks to about 80° C. and then slowly dip the preheated blocks into the gel solution (also at about 80° C.) such that the solution has time to "wick" into the microporosity of the blocks thus preventing entrapment of air bubbles. As the solution wicks into the block, it is gradually lowered into solution while keeping the wetted zone at or above the liquid level. Following this dip submersion into the hot solution, each block is laid on a folded paper towel in an 80° oven to drain out most of the macropore-filling solution. Over a period of about five minutes, each block is moved to a dry area to resume drainage (2–3 times). This method does not retain a detrimental amount of excess solution when the block is removed from the oven for cool-down allowing the solution to gel followed by dry down in ambient air or with dry nitrogen. By allowing the block to cool to room temperature, the solution gels and prevents mass migration of the gelatin during drying.

Dried gelatin is resorbable in water or body fluids at body temperature. As it hydrates and dissolves, it will rapidly lose strength and eventually be completely resorbed. The rate at which the gelatin that is dried down in the microstructure will react with body fluids, for example, is not quantified, but for most indications the gelatin should be crosslinked to slow down and control its rate of resorption.

There are a number of ways to produce crosslinking. These include but are not limited to controlled heat treatment with or without vacuum, exposure to UV light or x-rays, and chemical "tanning" treatments such as with glutaraldehyde. Less preferred would be irradiation, with the effective dose in the range of 20–30 Mrad.

A more preferred crosslinking method, the dehydrothermal method, involves superdehydration by a combination of vacuum and heat as discussed in U.S. Pat. No. 4,280,954 (incorporated by reference herein). Gelatin normally retains some 100 bound moisture at ambient conditions. To effect the dehydrothermal crosslinking, the moisture content has to be lowered to about 0.1%.

To fabricate coralline hydroxyapatite strengthened with polylactic acid lightly coating the walls of the macroporosity and filling some or all of the microporosity, the blocks (or other suitable shapes) of coralline hydroxyapatite (such as Interpore 200 or Pro Osteon® 500) is prepared as desired and dried in a desiccator with vacuum, for example at 20° or 30° for 10–15 hr. or more over $P_2O_5$ using blocks which have been predried at 160° C. at atmospheric pressure for at least 12 hours. A small wire frame such as a grid is used to support the porous hydroxyapatite samples to be infiltrated by the polylactic acid or other polymer. A catalyst such as tin (II) Octoate (Sn(II) (2-Ethylhexanoate)2) is loaded into a container on a wire grid by heating the catalyst in contact with the container grid or frame. The frame is placed in a container with a block of coralline hydroxyapatite thereon. The container also holds the lactic acid or other monomer such as ((3,5)-cis3, 6-Dimethyl-1,4 Dioxane-2,5-Dione (Aldrich), or other suitable monomer to make a biocompatible polymer. The block of coralline hydroxyapatite is held above the frame.

The container is sealed under dry nitrogen, heated and swirled to mix the catalyst and monomer and then positioned to allow the molten mixture to be absorbed by capillary action into the porosity of the coralline hydroxyapatite provided that heating is above the monomer melting point. The porous hydroxyapatite absorbs the monomer-catalyst mixture and is then heated at a temperature sufficient to ensure polymerization. Mechanical testing and examination of the polymer impregnated blocks under scanning electron microscopy demonstrated a significant increase in strength and that the macropores had their walls only lightly coated.

The following examples are illustrative of the practice of the invention, and are not intended to be limiting.

EXAMPLES

Example I

Experiments have been completed that establish a greater than four-fold compression strength increase, and a marked improvement in toughness and handling properties of ProOsteon® 500 and Interpore® 200. Screening experiments have been run using Kodak Bovine gelatin, bloom strength 260 (Kodak Catalog No. 137 6383). Aqueous solutions of gelatin have been prepared at 5%, 10%, 15%, 18%, 20% and 23% by dissolving gelatin in distilled water heated at 80° C. Solutions are prepared and used in a moisture-saturated oven. The saturated humidity is maintained by keeping a distilled water filled petri dish in the vacuum oven at atmospheric pressure. The vacuum oven is used because its tight closure, which facilitates humidity control. Unless the gel solution is in a humid environment, a thick "skin" rapidly forms, caused by water evaporation from the solution's surface. Such a skin changes the composition of the solution and interferes with the treatment of the HA.

Most of the preliminary tests were made with 10×10×45 mm ProOsteon® 500 blocks. Each individual block was given an identifying mark, weighed, and brought to treatment temperature by sealing it in a bottle and placing it in an 80° C. oven for at least one-half hour. This heat soak prevented the hot gel solution from gelling before it had time to penetrate the block. Sealing the parts in a bottle prevented premature uptake of moisture.

Table I summarizes averaged results for a recent round of tests of materials made in accordance with the invention (four blocks per test).

TABLE I

Result Summary for Gel Impregnation
of 10 × 10 × 45 mm IP500 by Dip/Drain Method

|  | 5% Gel Solution | 10% Gel Solution | 15% Gel Solution |
| --- | --- | --- | --- |
| Weight Gain dry Gel | 2.2% | 5.7% | 9.5% |
| Strength Increase versus Control | 1.8X | 2.8X | 4.2X |
| Compression Strength psi/MPa | 1138/7.8 | 1814/12.5 | 2680/18.5 |

Example II

A test using a gel solution derived from the high purity collagen was also carried out as follows: 100 ml of a 10% solution by steam autoclaving the fibrous collagen. The gelatin had a white turbid appearance. At 80° C., the solution was extremely fluid but retained the white turbidity. Five ProOsteon® 500 blocks (10×10×45 mm) were treated by wetting and dipping them into the solution. The solution rapidly wicked into each block at a rate faster than has been observed for the equivalent concentration Kodak gel solutions. The average air dry gelatin weight gain was 7.9%. The blocks retained their whiteness unlike the commercial gel treated samples that took on characteristic amber cast. Although no compressive strength measurements have been made on these samples, the hand break strength appears comparable to earlier reinforced preparations.

Example III

To determine whether the gelatin imparted the strength enhancement by infiltrating the microporosity, thereby forming a true composite as hoped for, or by merely stiffening the material by acting as a surface coating on the walls of the macropores, a fluorescamine stain (Sigma), which would make the gelatin fluorescent under UV illumination, was used. Areas of the treated HA-containing gelatin fluoresce while regions that have not been penetrated by gelatin do not fluoresce. One polished block ProOsteon® 500 treated by pipette with 15% gel solution and having 2.1% dry gel weight gain was "stained" by dipping the polished surface in a 2% solution of Fluorescamine in DMSO. When examined under a fluorescence microscopy, the gel was clearly distributed throughout the regions that otherwise appeared to by hydroxyapatite. FIG. 1 shows a photomicrograph of a sample infiltrated with gelatin.

Example IV

Because there was the slight possibility that gelatin might have been smeared across the surface during the dry polishing in the above stain experiment, it was decided to crosscheck the fluorescent stain results as follows:

A 10×10×45 mm ProOsteon® 500 block that was impregnated with 15% Kodak gel solution and a 5×15×41 mm block of Interpore® 200 that was impregnated with 15% gel solution were soaked in a 1% glutaraldehyde solution for five days to chemically crosslink the gelatin and prevent it from smearing during polishing. These "tanned" blocks were rinsed in distilled water, dried and sliced on a diamond cutoff saw. The fresh cut surfaces were ground and polished to a 5 µm diamond polish.

Figure 2:
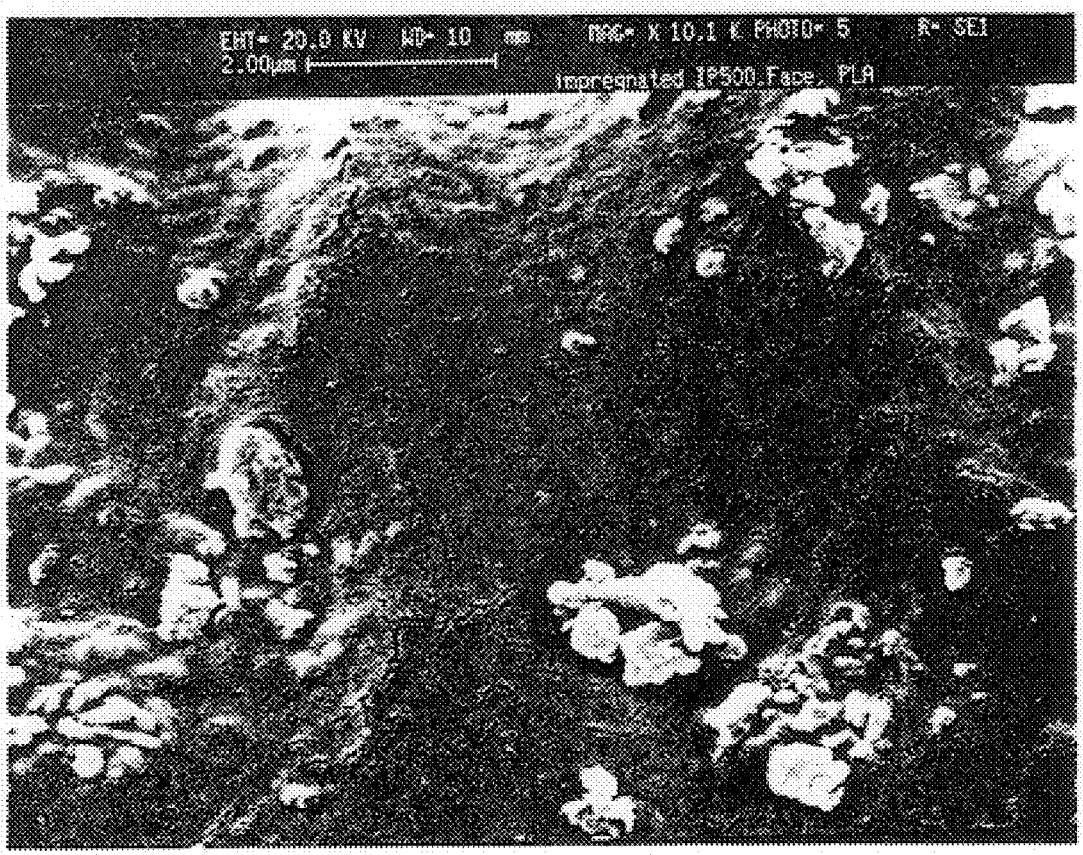
FIG. 2 is a photomicrograph (10,00×magnification) of a section of a porous hydroxyapatite sample infiltrated with a biopolymer in accordance with the present invention.

The samples were stained with fluorescamine and examined under fluorescent light microscopy. Results clearly showed that the gelatin had penetrated the microscopy of both the ProOsteon® 500 and Interpore® 200 blocks. FIG. 2 is a photomicrograph of a sample infiltrated with gelatin and crosslinked with glutaraldehyde.

Example V

Approximately 12 mg. of stannous octoate (Sn(II) (2-Ethylhexanoate)2) was placed on the bottom of each of two 28×10–8 mm vials (Fisher) along with a small wire frame. The vials were dried at 150° C. for two hours. The hot vials were removed from the oven and covered loosely with rubber lined Bakelite caps. The still hot vials were then transferred to a desiccator at 23° C. and exposed to 10.0× 10–3 mm Hg vacuum for four hours, at which point the desiccator was filled with dry nitrogen and the caps were quickly tightened upon the vials. The catalyst loaded wire frame equipped vials were tared and then transferred into a dry nitrogen filled glove bag. The dry nitrogen filled glove bag was equilibrated with $P_2O_5$. The catalyst loaded wire frame equipped vials were loaded with approximately 6.0 grams of monomer (2S)-cis-3,1-Dimethyl-1,4-Dioxane-2,5-Dione (Aldrich). The vials were placed inside of a desiccator over $P_2O_5$ with the caps loosely in place, and exposed to 10.0×10–3 mm Hg vacuum for 18 hrs. to dry the monomer. Following this, the monomer and catalyst loaded wire frame equipped vials were equilibrated with dry nitrogen inside of the desiccator, and the caps were quickly secured as the vials were transferred into a dry nitrogen glove bag.

Four coralline hydroxyapatite blocks 10×10×45 mm (ProOsteon® Implant 500) were weighed (3.7 to 4.5 grams) and dried at 150° C. for 14 hrs. The still hot blocks were individually packaged in hot oven dried vials. The vials in turn were placed into a desiccator at 23° C. over $P_2O_5$ for 14 hours at 10.0×10–3 mm Hg vacuum, with caps loosely in place. The desiccator was then equilibrated with dry nitrogen. The caps were quickly tightened on the vials as they were transferred from the desiccator to a dry nitrogen filled glove bag. The nitrogen inside the glove bag was exposed to $P_2O_5$ for several hours to insure anhydrous conditions, and each of the catalyst loaded wire frame equipped vials received two dry coralline hydroxyapatite blocks. The weight of each block was then written upon the corresponding fully loaded vials after the cap was secured. The two vials were randomly labeled A and B. It is imperative that the wire frames are designed such that the blocks are supported above the monomer, and do not touch the monomer and catalyst in the bottom of the vial. The two fully loaded vials were then removed from the glove bag.

The two fully loaded sealed vials were placed upright into a 130° C. oven until the monomer had just melted (15 minutes) and then the vials were swirled for five minutes to mix the monomer with the catalyst. When the blocks were completely saturated, the vials were placed upright again to drain out any excess monomer from the blocks. The blocks were then curred to 96 hrs. at 145° C.

Figure 5:
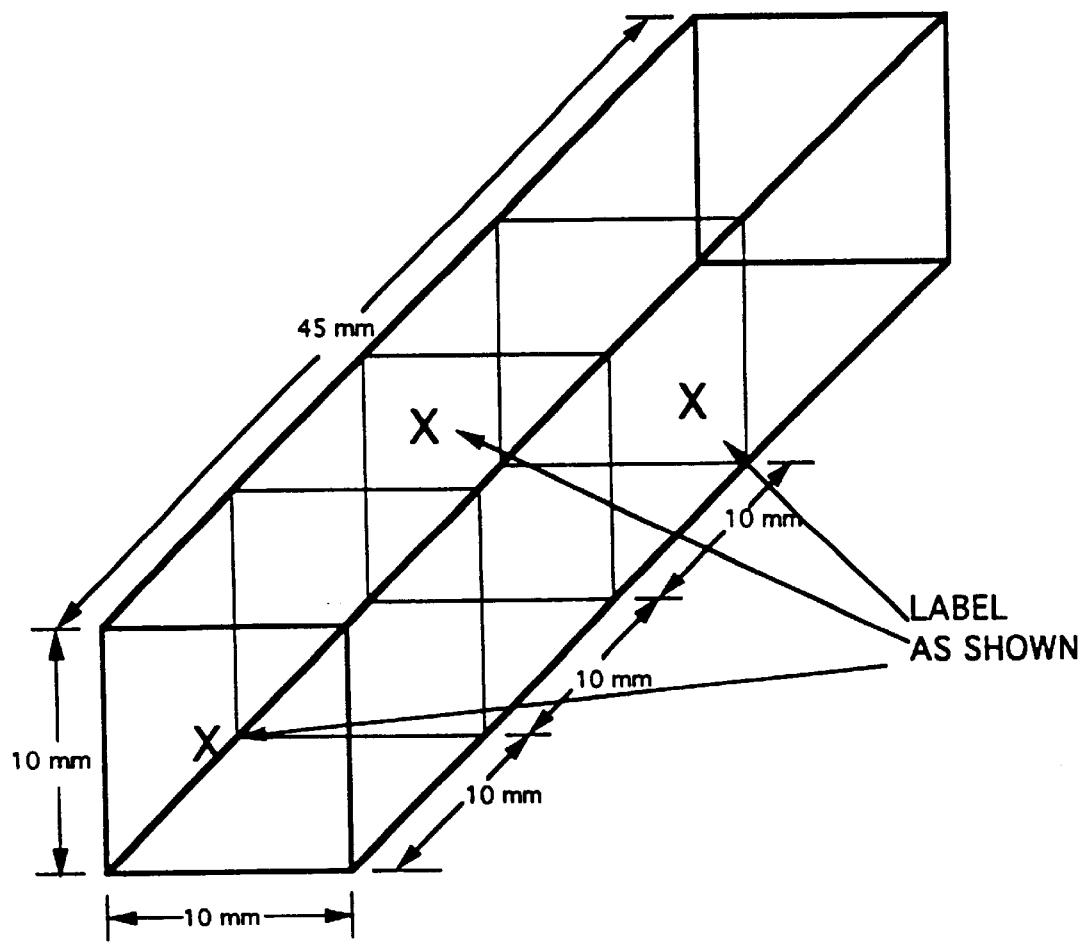
FIG. 5 is a schematic diagram showing the manner in which the coralline hydroxyapatite block was cut for mechanical testing.

The two 10×10×45 mm coralline hydroxyapatite blocks, which were impregnated with Polylactic acid (PLA), were cut into three 1 cm cubes for mechanical testing. The remaining 1×1×1.5 cm block was kept for descriptive analysis. The three cubes from each block were marked with a pen on three orthogonal axes as shown in FIG. 5. The three cubes from two of the blocks were soaked with distilled water for twenty-four hours before being compression tested on a Carver press equipped with a force gauge with full scale deflection of 500 lb. The blocks were oriented with the marked side facing up, and 1×15×15 mm balsa wood shims were placed on either side of the blocks during the compression test to insure even distribution of stress. The three cubes from the other two blocks were tested in a similar fashion, in a dry state. Two untreated coralline hydroxyapatite control blocks were tested in an identical fashion as the four PLA impregnated blocks, one dry and one wet. The results from these tests are contained in Table II. The wet HA-PLA cubes have a 5.15-fold increase in compressive strength over untreated wet controls. Literature values for the controls are 40–60 lb/cm2 (1.8–2.7 Mpa) (Tencer et al.).

TABLE II

| CUBE | control dry | control wet | HA-PLA dry C-29-V-A | HA-PLA wet C-29-V-B | HA-PLA dry C-29-V-A | HA-PLA wet C-29-V-B |
|---|---|---|---|---|---|---|
| Lb/cm2 (1.00 lb/cm$^2$ = 0.044 MPa) Strength | | | | | | |
| 1 | 225 | 05 | 320 | 25 | 200 | 150 |
| 2 | 10 | 100 | 205 | 180 | 430 | 470 |
| 3 | 5 | 05 | 465 | 45 | 205 | 275 |
| MEAN | 80 | 37 | 330 | 83 | 278 | 298 |

Figure 3:
FIG. 3 is a scanning electron photomicrograph (5000× magnification) of the face of a non-impregnated specimen.
Figure 4:
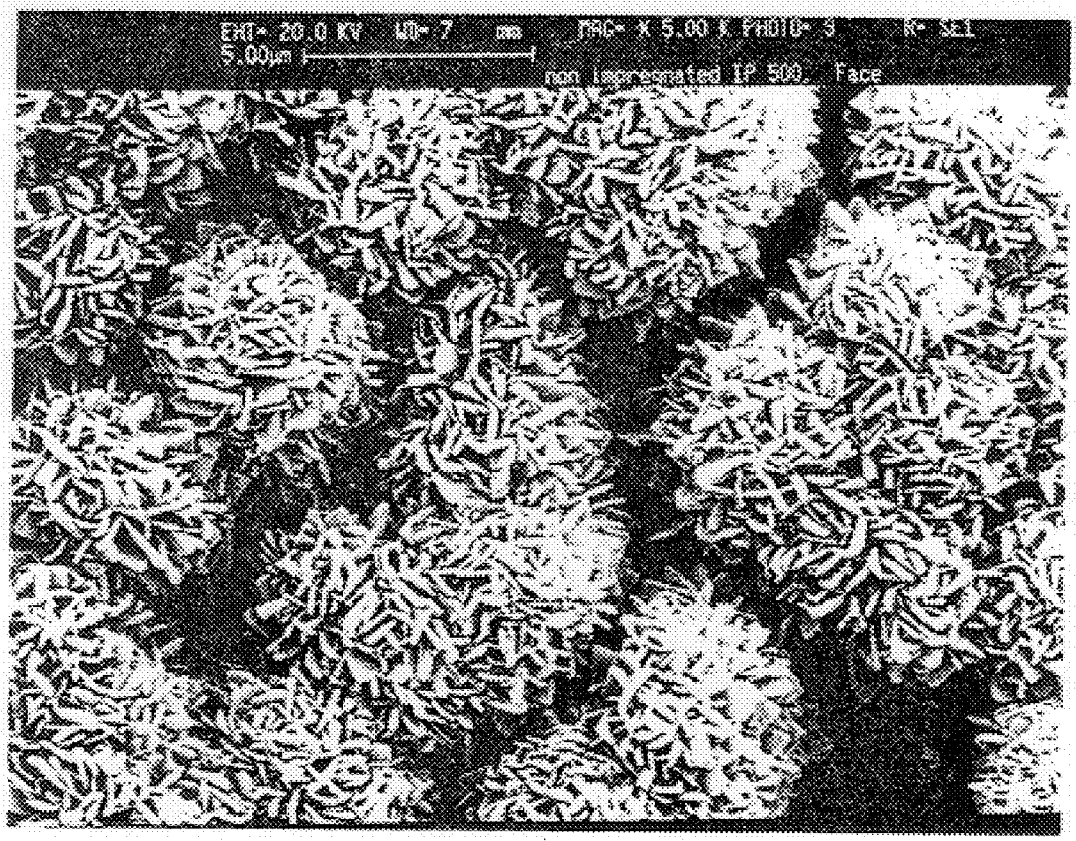
FIG. 4 is a scanning electron photomicrograph at a magnification of 5000×of the face of a non-impregnated specimen.

Scanning electron micrographs (FIGS. 3,4) show that the polymer provides only a limited coating. The coating appears by scanning electron microscopy to be less then 5 µm in thickness. The white hydroxyapatite crystallites on the surface of the macropores can be seen protruding through the thin polymer coating. The control photographs (FIGS. 5,6) show the untreated hydroxyapatite by way of reference. Fluorescence microscopy using a fluorescein labeled polylactic acid stain indicate that the polymer is contained primarily within the micropores.

The manufacture of a composite employing the in situ polymerization of the monomer L-Lactide (3(S)-cis-3,6-Dimethyl-1,4-Dioxane-2,5-Dione), 0.2% of the catalyst Tin Octoate (Sn-II, (2-Ethyl Hexanoate)2), and 10×10×45 mm coralline hydroxyapatite blocks resulted in a material having superior compressive strength, without significant sacrifice of macropores (according to SEM), compared to the control. Compressive strengths of at least five-fold over the untreated blocks have been realized using the methods described herein as compared to the untreated material. The superiority of the method described herein is attributed to the filling of the microporosity with polymer.

Example VI

Additionally, a method was developed which utilizes glycolide monomer (1,4-dioxane-2,5-dione) to impregnate ProOsteon® blocks in a substantially similar fashion. The melting point of glycolide monomer is 83° C. The lower melting point (relative to lactide) coupled with the higher reactivity of glycolide with the catalyst (Sn-II octoate) allows the process to procede at lower temperatures. Similarly, co-polymers of lactide and glycolide may be used to achieve intermediate results.

Of course, other modifications, alterations and substitutions may be apparent to those skilled in the art in light of the foregoing disclosure. Therefore it is intended that the scope of the invention be governed by the following claims.

We claim:

1. A method of strengthening a porous ceramic biomaterial which comprises:
   a) preparing a biomonomer polymerizable mixture or solution; and
   b) infiltrating micropores and macropores included in the porous ceramic biomaterial with the biocompatible, polymerizable mixture or solution under conditions wherein the mixture or solution will polymerize in the micropores and only minimally coat interior passages of the macropores with polymer while substantially filling the micropores.

2. A method in accordance with claim 2, wherein the microporous biomaterial is coralline hydroxyapatite or reticulated foam ceramic.

3. A method in accordance with claim 1 wherein the biocompatible polymerizable mixture contains lactide or a derivative thereof and the polymer formed by polymerization is a polylactic acid or derivative thereof.

4. A method in accordance with claim 1 wherein the biocompatible polymerizable mixture or solution contains glycolide or a derivative thereof and the polymer formed by polymerization is polyglycolic acid or a derivative thereof.

5. A method in accordance with claim 1 wherein a catalyst is added to the biocompatible polymerizable mixture or solution before the biocompatible, polymerizable mixture or solution infiltrates the porous ceramic biomaterial.

6. A method in accordance with claim 5 wherein the monomer is lactide, glycolide, a co-polymer or a derivative.

7. An improved biomaterial comprising:
   a hydroxyapatite structure having a substantially uniform three dimensional porosity connected to an exterior surface of the biomaterial, said porosity including interconnected macropores having diameters in the range from about 100 microns to about 1000 microns, and micropores having pore sizes of about 1 micron or less, the macropores and micropores of said biomaterial infiltrated with a biocompatible polymer such that the biocompatible polymer covers interior walls and passageways of the macropores of the biomaterial substantially without filling the macropores but substantially filling the micropores contained in the biomaterial.

8. An improved biomaterial in accordance with claim 7, wherein the hydroxyapatite structure is derived from coral or a ceramic material having interconnected porosity, and the polymer is polymerized within the porosity of the hydroxyapatite structure.

9. A dental prosthesis comprising the improved biomaterial in accordance with claim 8.

10. An orthopedic prosthesis comprising the improved biomaterial in accordance with claim 8.

11. A plastic surgery prosthesis comprising the improved biomaterial in accordance with claim 8.

12. An ear, nose and throat prosthesis comprising the improved biomaterial in accordance with claim 8.

13. A neurosurgery prosthesis comprising the improved biomaterial in accordance with claim 8.

14. A podiatric prosthesis comprising the improved biomaterial in accordance with claim 8.

15. A bone void filler comprising the improved biomaterial in accordance with claim 7, wherein the bone void filler comprises granules.

16. A bone void filler comprising the improved biomaterial in accordance with claim 8.

17. A bone void filler comprising the improved biomaterial in accordance with claim 7, wherein the bone void filler is a block.

18. A method of replacing bone tissue in an organism comprising:

locating the void in or adjacent to bone to be filled, and implanting the biomaterial according to claim 8 into the organism under conditions which permit bone tissue to grow into the macroporosity of the biomaterial in order that the biomaterial can be integrated substantially into the skeletal system of the organism.

19. A composition of material useful as an interconnected porosity including micropores and macropores, at least some of said macropores open to said surface and interconnected with one another;

the macropores substantially coated and the micropores substantially filled by a polylactic acid polymer, polyglycolic acid polymer, or co-polymer thereof, the polymer polymerized in situ from a lactide or glycolide monomer or mixture thereof introduced into the porosity of the porous hydroxyapatite structure under conditions which cause polymerization in the microporosity and macroporosity of the material.

20. A composition in accordance with claim 19 wherein the monomer mixture additionally includes a polymerization catalyst.

21. A composition in accordance with claim 19 wherein the polymerization catalyst is stannous octoate.

22. A method of making a biomaterial, comprising:

providing a porous coralline hydroxyapatite or synthetic porous ceramic structure having an internal porosity including micropores and macropores, with at least some of the macropores interconnected through internal passageways and open to an outer surface of the structure;

introducing into the porosity a monomer mixture or solution containing lactide, glycolide or mixtures thereof under conditions wherein the monomer mixture or solution fills the microporosity substantially without filing the macroporosity in the structure, and polymerizing the monomer mixture or solution in situ into a polylactic acid or polyglycolic acid polymer or copolymer under polymerizing conditions.

23. A method in accordance with claim 22, further comprising introducing a catalyst into the mixture or solution prior to polymerization porosity of the structure polymerization.

24. A method in accordance with claim 23, wherein said catalyst is stannous octoate.

25. A method in accordance with claim 23, wherein said monomer mixture or solution is introduced into said porosity using capillary action.

26. A method in accordance with claim 22, wherein the viscosity of the lactide or glycolide monomer mixture or solution permits the mixture or solution to infiltrate the porosity of the structure by capillary action.

27. A method for strengthening a porous ceramic biomaterial having micro porosity and macroporosity, comprising:

providing the porous ceramic biomaterial; and infiltrating the porosity of the porous ceramic biomaterial with a liquid biocompatible polymer under conditions wherein the polymer infiltrates the porosity of the porous ceramic biomaterial, substantially filing micropores contained therein while coating walls of the macroporosity, minimally without filing the macroporosity.

* * * * *